United States Patent
Legeai-Mallet et al.

(10) Patent No.: US 11,951,090 B2
(45) Date of Patent: Apr. 9, 2024

(54) METHODS AND PHARMACEUTICAL COMPOSITIONS FOR THE TREATMENT OF FGFR3-RELATED CHONDRODYSPLASIAS

(71) Applicants: INSERM (INSTITUT NATIONAL DE LA SANTÉ ET DE LA RECHERCHE MÉDICALE), Paris (FR); UNIVERSITE DE PARIS, Paris (FR); FONDATION IMAGINE, Paris (FR); ASSISTANCE PUBLIQUE-HÔPITAUX DE PARIS (APHP), Paris (FR); UNIVERSIDAD DE GRANADA, Grandada (ES)

(72) Inventors: Laurence Legeai-Mallet, Paris (FR); Antonio Segura Carretero, Granada (ES); Maria De La Luz Cadiz Gurrea, Granada (ES)

(73) Assignees: INSTITUT NATIONAL DE LA SANTÉ ET DE LA RECHERCHE MÉDICALE, Paris (FR); UNIVERSITÉ DE PARIS, Paris (FR); FONDATION IMAGINE, Paris (FR); ASSISTANCE PUBLIQUE-HÔPITAUX DE PARIS, Paris (FR); UNIVERSIDAD DE GRANADA, Granada (ES)

( * ) Notice: Subject to any disclaimer, the term of this patent is extended or adjusted under 35 U.S.C. 154(b) by 672 days.

(21) Appl. No.: 16/964,781

(22) PCT Filed: Jan. 23, 2019

(86) PCT No.: PCT/EP2019/051622
§ 371 (c)(1),
(2) Date: Jul. 24, 2020

(87) PCT Pub. No.: WO2019/145356
PCT Pub. Date: Aug. 1, 2019

(65) Prior Publication Data
US 2021/0052546 A1    Feb. 25, 2021

(30) Foreign Application Priority Data
Jan. 24, 2018 (EP) ..................... 18305053

(51) Int. Cl.
*A61K 31/353* (2006.01)
*A61P 19/00* (2006.01)

(52) U.S. Cl.
CPC ............ *A61K 31/353* (2013.01); *A61P 19/00* (2018.01)

(58) Field of Classification Search
None
See application file for complete search history.

(56) References Cited

FOREIGN PATENT DOCUMENTS

WO    2016/046375 A1    3/2016

OTHER PUBLICATIONS

Andujar et al: "Cocoa Polyphenols and Their Potential Benefits for Human Health", Oxidative Medicine and Cellular Longevity, vol. 5, No. 1, pp. 17-23, Jan. 1, 2012.
Benoist-Lasselin et al: "Huma immortalized chondrocytes carrying heterozygous FGFR3 mutations: An in vitro model to study chondrydysplasias", FEBS Letters, vol. 581, No. 14, pp. 2593-2598, May 31, 2007.
Fernandex-Arroyo et al: "The impact of polyphenols on chondrocyte growth and survival: a preliminary report", Food and Nutrition Research, vol. 59, No. 1, Jan. 1, 2015.

*Primary Examiner* — Samantha L Shterengarts
(74) *Attorney, Agent, or Firm* — WCF IP

(57) ABSTRACT

FGFR3-related chondrodysplasias represent a group of rare diseases. Among them, achondroplasia, a nonlethal form of chondrodysplasia, is the most common type of dwarfism. The mutation, which produce an increase of FGFR3 function, affects many tissues, most strikingly the cartilaginous growth plate and bone in the growing skeleton, leading to a variety of manifestations and complications. In attempt to find a new therapeutic approach for FGFR3-related chondrodysplasia, the inventors purified (−)-epicatechin from *T. cacao* and showed that (−)-epicatechin treatment significantly increases the length of the $Fgfr3^{Y367C/+}$ femurs comparing to $Fgfr3^{+/+}$ femurs and improves the whole growth plate cartilage. The present invention thus relates to the use of (−)-epicatechin for the treatment of FGFR3-related chondrodysplasias.

1 Claim, 16 Drawing Sheets

Figure 1A:
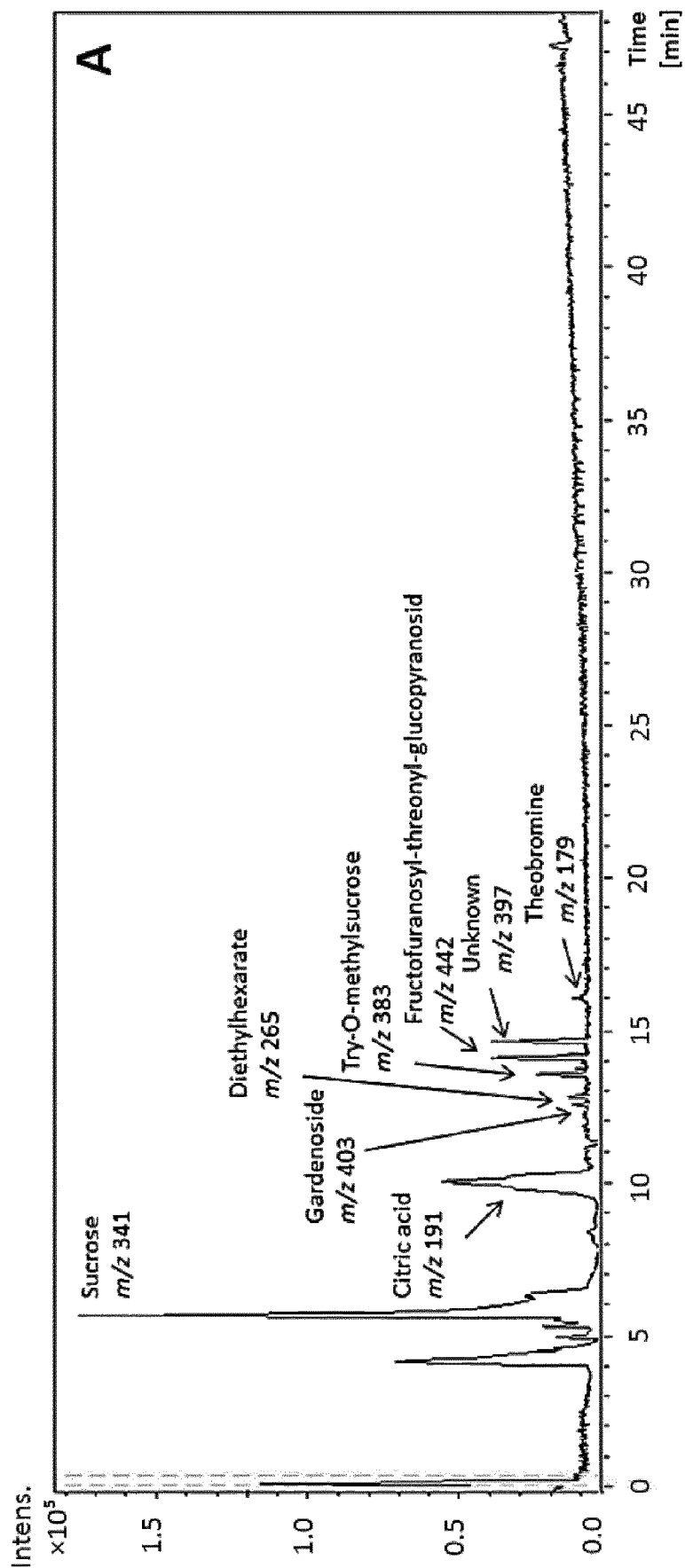
Figure 1B:
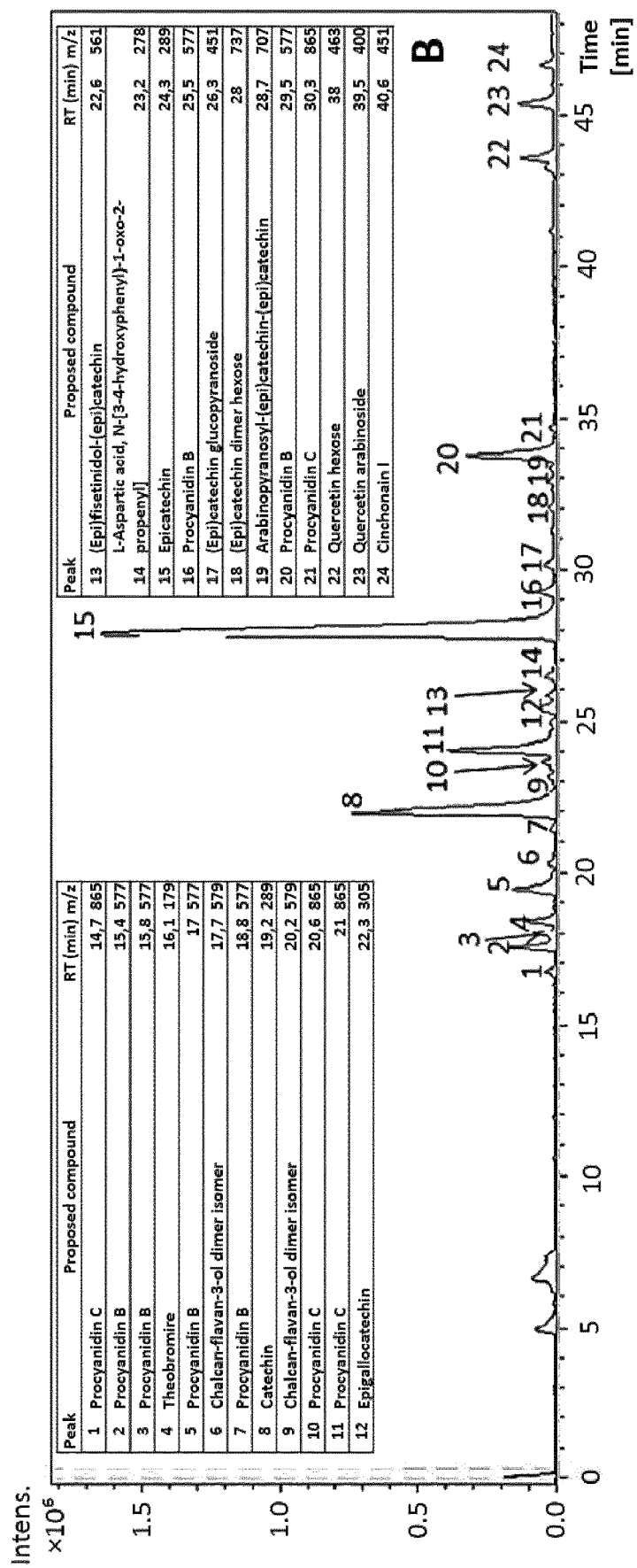
Figure 1C:
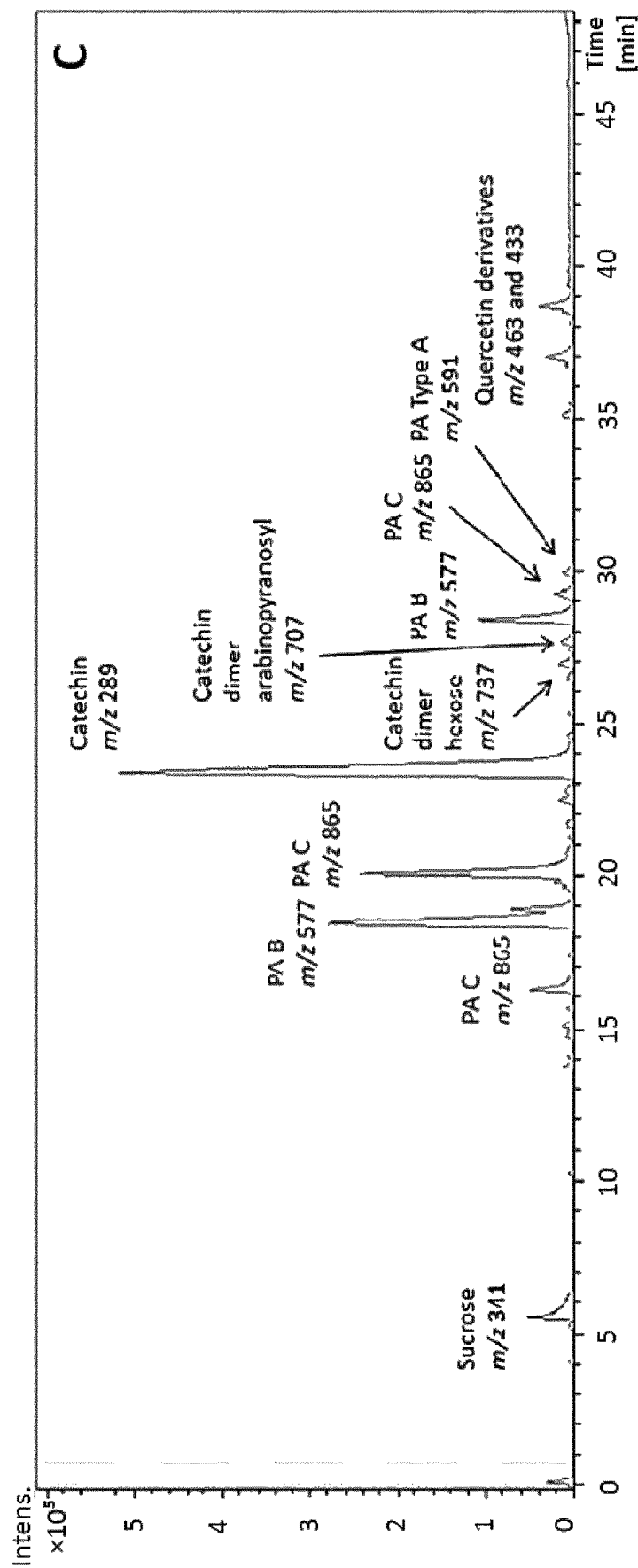
Figure 1D:
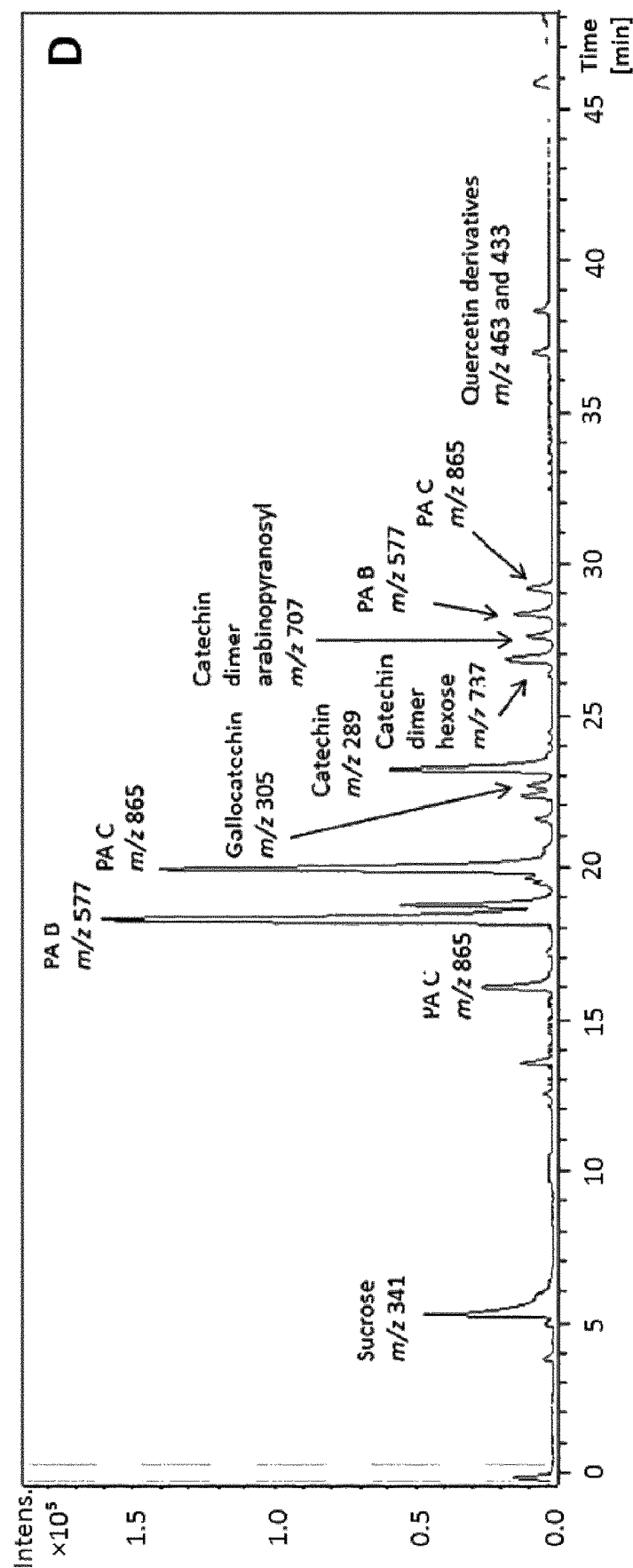
Figure 1E:
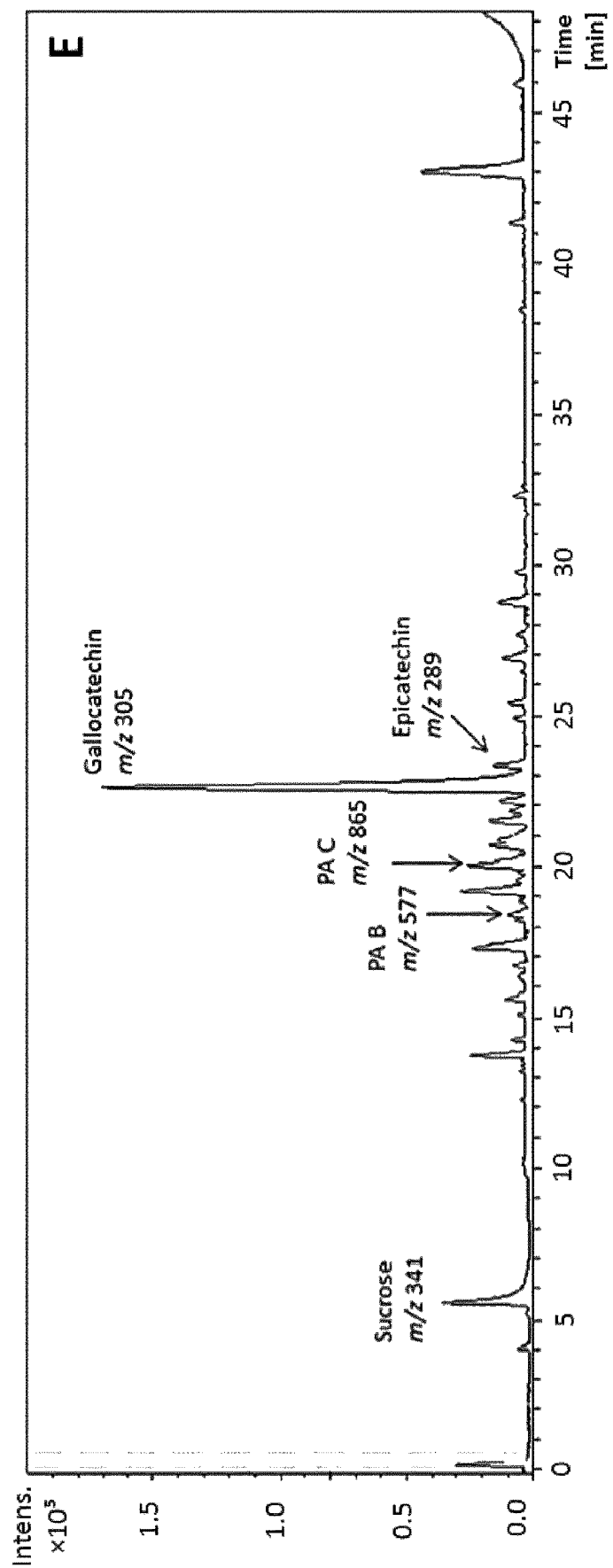

METHODS AND PHARMACEUTICAL COMPOSITIONS FOR THE TREATMENT OF FGFR3-RELATED CHONDRODYSPLASIAS

FIELD OF THE INVENTION

The present invention relates to methods and pharmaceutical compositions for the treatment of FGFR3-related chondrodysplasias.

BACKGROUND OF THE INVENTION

"Rare diseases" are diseases with a particularly low prevalence. In this manner, the European Union considers diseases to be rare when they affect not more than 5 per 10,000 persons (Rodwell and Ayme, 2014a). As example, achondroplasia presents an estimated prevalence of 2.6 per 100,000 persons in EU (Orphanet, 2014). In this sense, rare diseases were defined for first time in EU Regulation (EC) No 141/2000 (*Regulation (EC) No 141/2000 of the European Parliament and of the Council of 16 Dec. 1999 on orphan medicinal products*). In general, patients with rare diseases are particularly isolated and psychologically, socially, economically and culturally vulnerable, with a lack of specific health policies for these diseases and the scarcity of expertise, translate into delayed diagnosis and difficult access to care, inadequate or even harmful treatments and loss of confidence in the health care system (Orphanet, n.d.; Rodwell and Ayme, 2014b).

Receptor tyrosine kinases (RTKs) are cell surface receptors contributing to cell signalling, but some mutations on these receptors are associated to specific rare diseases. RTKs play pivotal roles in development, tissue repair and normal cellular homeostasis as well as mediate cellular responses to a broad array of extracellular signals involved in the regulation of cell proliferation, migration, differentiation and survival signalling. This RTKs type plays an essential role in the regulation of homeostasis of the cartilage e.g. chondrocyte differentiation, proliferation and apoptosis, and is required for normal skeleton development as well as regulation of both osteogenesis and postnatal bone mineralization by osteoblasts (UniProt, n.d.). Achondroplasia, a non-lethal form of chondrodysplasia, is the most common type of dwarfism. It is mostly due to de novo mutation and has an autosomal dominant inheritance (Rousseau et al., 1994; Di Rocco et al., 2014). The mutation, which produce an increase of FGFR3 function, affects many tissues, most strikingly the cartilaginous growth plate and bone in the growing skeleton, leading to a variety of manifestations and complications. As other RTKs, the binding of the ligand, that is fibroblast growth factors (FGFs), leads to dimerization and transautophosphorylation, resulting in the stimulation of its tyrosine kinase activity (Huete et al., 2011). At molecular levels, four main signalling pathways for FGFR3 may be implicated: signal transducer and activator of transcription 1 (STAT1), mitogen activated protein kinase (MAPK), phospholipase C γ (PLCγ), and phosphatidylinositol phosphate-3-kinaseserine/threonine kinase (PI3K-AKT; protein kinase B) and others. (Horton et al., 2007, Ornitz D M & Legeai-Mallet L 2017).

Cocoa (*Theobroma cacao*) is a major, economically important, international crop, which has been related to several nutritional benefits including high antioxidant capacity. These healthy properties have been associated with the phenolic fraction (Andújar et al., 2012; Cádiz-Gurrea et al., 2015). The main subclass of flavonoids found in cocoa is flavanols, particularly (epi)catechins monomers, and their oligomers, also known as procyanidins which range from dimers to decamers (Cádiz-Gurrea et al., 2014). This extract has been reported to show an inhibitory effect of both FGFR3 activated with FGF2 ligand and the phosphorylation cascade related to FGFR3 signalling (Legeai-Mallet and Segura-Carretero, 2015 and WO2016046375).

SUMMARY OF THE INVENTION

The present invention relates to methods and pharmaceutical compositions for the treatment of FGFR3-related chondrodysplasias. In particular, the present invention is defined by the claims.

DETAILED DESCRIPTION OF THE INVENTION

The present invention relates to a method of treating a FGFR3-related chondrodysplasia in a patient in need thereof consisting in administering to the subject a therapeutically effective amount of a substantially pure (−)-epicatechin.

The present invention also relates to a pharmaceutical composition comprising a therapeutically effective amount of a substantially pure (−)-epicatechin for use in a method of treating a FGFR3-related chondrodysplasia in a patient in need thereof.

As used herein, the term "FGFR3-related chondrodysplasia" is intended to mean a skeletal disease that is caused by an abnormal increased activation of FGFR3, in particular by expression of a constitutively active mutant of the FGFR3 receptor, in particular a constitutively active mutant of the FGFR3 receptor as described after. As used herein, the terms "FGFR3", "FGFR3 tyrosine kinase receptor" and "FGFR3 receptor" are used interchangeably throughout the specification and refer to all of the naturally-occurring isoforms of FGFR3. As used herein, the expressions "constitutively active FGFR3 receptor variant", "constitutively active mutant of the FGFR3" or "mutant FGFR3 displaying a constitutive activity" are used interchangeably and refer to a mutant of said receptor exhibiting a biological activity (i.e. triggering downstream signaling), and/or exhibiting a biological activity which is higher than the biological activity of the corresponding wild-type receptor in the presence of FGF ligand. A constitutively active FGFR3 variant according to the invention is in particular chosen from the group consisting of (residues are numbered according to their position in the precursor of fibroblast growth factor receptor 3 isoform 1-806 amino acids long-): a mutant wherein the serine residue at position 84 is substituted with lysine (named herein below S84L); a mutant wherein the arginine residue at position 248 is substituted with cysteine (named herein below R200C); a mutant wherein the arginine residue at position 248 is substituted with cysteine (named herein below R248C); a mutant wherein the serine residue at position 249 is substituted with cysteine (named herein below S249C); a mutant wherein the proline residue at position 250 is substituted with arginine (named herein below P250R); a mutant wherein the asparagine residue at position 262 is substituted with histidine (named herein below N262H); a mutant wherein the glycine residue at position 268 is substituted with cysteine (named herein below G268C); a mutant wherein the tyrosine residue at position 278 is substituted with cysteine (named herein below Y278C); a mutant wherein the serine residue at position 279 is substituted with cysteine (named herein below S279C); a mutant wherein the glycine residue at position 370 is substituted with cysteine (named herein below G370C); a mutant wherein the serine residue at position 371 is substituted with cysteine (named herein below S371C); a mutant wherein the tyrosine residue at position 373 is substituted with cysteine (named herein below Y373C); a mutant wherein the glycine residue at position 380 is substituted with arginine (named herein below G380R); a mutant wherein the valine residue at position 381 is substituted with glutamate (named herein below V381E); a mutant wherein the alanine residue at position 391 is substituted with glutamate (named herein below A391E); a mutant wherein the asparagine residue at position 540 is substituted with Lysine (named herein below N540K); a mutant wherein the termination codon is eliminated due to base substitutions, in particular the mutant wherein the termination codon is mutated in an arginine, cysteine, glycine, serine or tryptophane codon (named herein below X807R, X807C, X807G, X807S and X807W, respectively); a mutant wherein the lysine residue at position 650 is substituted with another residue, in particular with methionine, glutamate, asparagine or glutamine (named herein below K650M, K650E, K650N and K650Q). Typically, a constitutively active FGFR3 variant according to the invention is K650M, K650E or Y373C mutant.

In some embodiments, the FGFR3-related skeletal diseases are FGFR3-related chondrodysplasias and FGFR3-related craniosynostosis. In some embodiments, the FGFR3-related skeletal osteochondrodysplasias correspond to an inherited or to a sporadic disease. As used herein, the term "FGFR3-related skeletal dysplasias" includes but is not limited to thanatophoric dysplasia type I, thanatophoric dysplasia type II, hypochondroplasia, achondroplasia and SADDAN (severe achondroplasia with developmental delay and acanthosis nigricans). In some embodiments, the FGFR3-related skeletal osteochondrodysplasia is caused by expression in the subject of a constitutively active FGFR3 receptor variant such as defined above. In some embodiments, the FGFR3-related chondrodysplasia is an achondroplasia caused by expression of the G380R constitutively active mutant of the FGFR3 receptor. In some embodiments, the FGFR3-related chondrodysplasia is a hypochondroplasia caused by expression of the N540K, K650N, K650Q, S84L, R200C, N262H, G268C, Y278C, S279C, V381E, constitutively active mutant of the FGFR3 receptor. In some embodiments, the FGFR3-related chondrodysplasia is a thanatophoric dysplasia type I caused by expression of a constitutively active mutant of the FGFR3 receptor chosen from the group consisting of R248C, S248C, G370C, S371C; Y373C, X807R, X807C, X807G, X807S, X807W and K650M FGFR3 receptors. In some embodiments, the FGFR3-related chondrodysplasia is a thanatophoric dysplasia type II caused by expression of the K650E constitutively active mutant of the FGFR3 receptor. In some embodiments, the FGFR3-related chondrodysplasia is a severe achondroplasia with developmental delay and acanthosis nigricans caused by expression of the K650M constitutively active mutant of the FGFR3 receptor. In some embodiments, the FGFR3-related craniosynostosis corresponds to an inherited or to a sporadic disease. In some embodiments, the FGFR3-related craniosynostosis is Muenke syndrome caused by expression of the P250R constitutively active mutant of the FGFR3 receptor or Crouzon syndrome with acanthosis nigricans caused by expression of the A391E constitutively active mutant of the FGFR3 receptor.

As used herein, the term "treatment" or "treat" refer to both prophylactic or preventive treatment as well as curative, improving the patient's condition or disease modifying treatment, including treatment of patient at risk of contracting the disease or suspected to have contracted the disease as well as patients who are ill or have been diagnosed as suffering from a disease or medical condition, and includes suppression of clinical relapse. The treatment may be administered to a subject having a medical disorder or who ultimately may acquire the disorder, in order to prevent, cure, delay the onset of, reduce the severity of, or ameliorate one or more symptoms of a disorder or recurring disorder, or in order to prolong the survival of a subject beyond that expected in the absence of such treatment. By "therapeutic regimen" is meant the pattern of treatment of an illness, e.g., the pattern of dosing used during therapy. A therapeutic regimen may include an induction regimen and a maintenance regimen. The phrase "induction regimen" or "induction period" refers to a therapeutic regimen (or the portion of a therapeutic regimen) that is used for the initial treatment of a disease. The general goal of an induction regimen is to provide a high level of drug to a patient during the initial period of a treatment regimen. An induction regimen may employ (in part or in whole) a "loading regimen", which may include administering a greater dose of the drug than a physician would employ during a maintenance regimen, administering a drug more frequently than a physician would administer the drug during a maintenance regimen, or both. The phrase "maintenance regimen" or "maintenance period" refers to a therapeutic regimen (or the portion of a therapeutic regimen) that is used for the maintenance of a patient during treatment of an illness, e.g., to keep the patient in remission for long periods of time (months or years). A maintenance regimen may employ continuous therapy (e.g., administering a drug at regular intervals, e.g., daily, weekly, monthly, yearly, etc.) or intermittent therapy (e.g., interrupted treatment, intermittent treatment, treatment at relapse, or treatment upon achievement of a particular predetermined criteria [e.g., disease manifestation, etc.]).

As used herein the term "(−)-epicatechin" has its general meaning in the art and refers to (2R,3R)-2-(3,4-dihydroxyphenyl)-3,4-dihydro-2H-chromene-3,5,7-triol. The methods of producing or extracting (−)-epicatechin are well known to the skilled person.

As used herein, the term "substantially pure" refers to the total absence, or near total absence, of impurities, such as related-substance impurities. For example, when a (−)-epicatechin composition is said to be substantially pure, there are either no detectable related-substance impurities, or if a single related-substance impurity is detected, it is present in an amount no greater than 0.1% by weight, or if multiple related-substance impurities are detected, they are present in aggregate in an amount no greater than 0.6% by weight.

Accordingly, the patient is administered with a pharmaceutical composition comprising the substantially pure (−)-epicatechin as active principle and at least one pharmaceutically acceptable excipient. As used herein the term "active principle" or "active ingredient" are used interchangeably. The active principle is used to alleviate, treat or prevent a medical condition or disease. By the term "pharmaceutically acceptable excipient" herein, it is understood a carrier medium which does not interfere with the effectiveness of the biological activity of the active ingredient(s) and which is not excessively toxic to the host at the concentration at which it is administered. Said excipients are selected, depending on the pharmaceutical form and the desired method of administration, from the usual excipients known by a person skilled in the art. In some embodiments, the pharmaceutical composition of the present invention does not comprise a second active principle. Accordingly, in some embodiments, the pharmaceutical composition of the present invention is not a *Theobroma cacao* extract as described in WO 2016046375. In some embodiments the pharmaceutical composition does not comprises an amount of flavonols, sweroside, and hexenyl 5 xylopyranosyl glucopyranoside. In some embodiments, the pharmaceutical composition of the present invention does not comprise an amount of procyanidin, catechin, cinchonain and derivatives thereof. In some embodiments, the pharmaceutical composition does not comprises an amount of 3,4-N-phenylpropenoyl-L-aminoacid or derivative thereof chosen from/V-caffeoyl-L-aspartate, L-Aspartic acid, A/-[3-(4-hydroxyphenyl)-1-oxo-2-propenyl], L-Aspartic acid, A/-[3-(4-hydroxy-3-methoxyphenyl)-1-oxo-2-propenyl], trans-clovamide (A/-[(2E)-3-(3,4-dihydroxyphenyl)-1-oxo-2-propen-1-yl]-3-hydroxy-L-tyrosine), deoxyclovamide (A/-[(2E)-3-(3,4-dihydroxyphenyl)-1-oxo-2-propen-1-yl]-tyrosine) and derivatives thereof. In some embodiments, the pharmaceutical composition of the present invention does not comprise a compound selected from the group consisting of quercetin, quercetin glucuronide, quercetin hexose, quercetin arabinoside and isomers thereof and/or said at least one procyanidin, catechin, cinchonain and derivative thereof chosen from proanthocyanidin A, (epi)catechin, (epi)catechin dimer hexose, arabinopyranosyl-(epi)catechin-(epi) catechin, (epi)gallocatechin, (epi)catechin glucopyranoside, catechin diglucopyranoside, cinchonain I, (epi)catechin tetramer, (epi)catechin pentamer, (epi)catechin hexamer, (epi)catechin methyl dimer, (epi)catechin ethyl dimer, procyanidin A, procyanidin B, procyanidin C and isomers thereof. In some embodiments, the pharmaceutical composition does not comprises an amount of procyanidin B; (epi)catechin tetramer; (epi)catechin pentamer; hexenyl xylopyranosyl glucopyranoside; (epi)catechin dimer hexose; arabinopyranosyl-(epi)catechin-(epi)catechin; -procyanidin C; -proanthocyanidin A; (epi)catechin ethyl dimer; quercetin; quercetin hexose; -cinchonain I; procyanidin A; and sweroside.

By a "therapeutically effective amount" of the substantially pure (−)-epicatechin as above described is meant a sufficient amount to provide a therapeutic effect. It will be understood, however, that the total daily usage of the substantially pure (−)-epicatechin will be decided by the attending physician within the scope of sound medical judgment. The specific therapeutically effective dose level for any particular subject will depend upon a variety of factors including the disorder being treated and the severity of the disorder; activity of the specific compound employed; the specific composition employed, the age, body weight, general health, sex and diet of the subject; the time of administration, route of administration, and rate of excretion of the specific compound employed; the duration of the treatment; drugs used in combination or coincidental with the specific polypeptide employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Typically, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

The invention will be further illustrated by the following figures and examples. However, these examples and figures should not be interpreted in any way as limiting the scope of the present invention.

FIGURES

FIG. 1. Different profiles of Sep-Pak fractions by HPLC-ESI-TOF-MS were; a) PA, b) PC, c) MN, d) OL and e) PL fractions.

Figure 2:
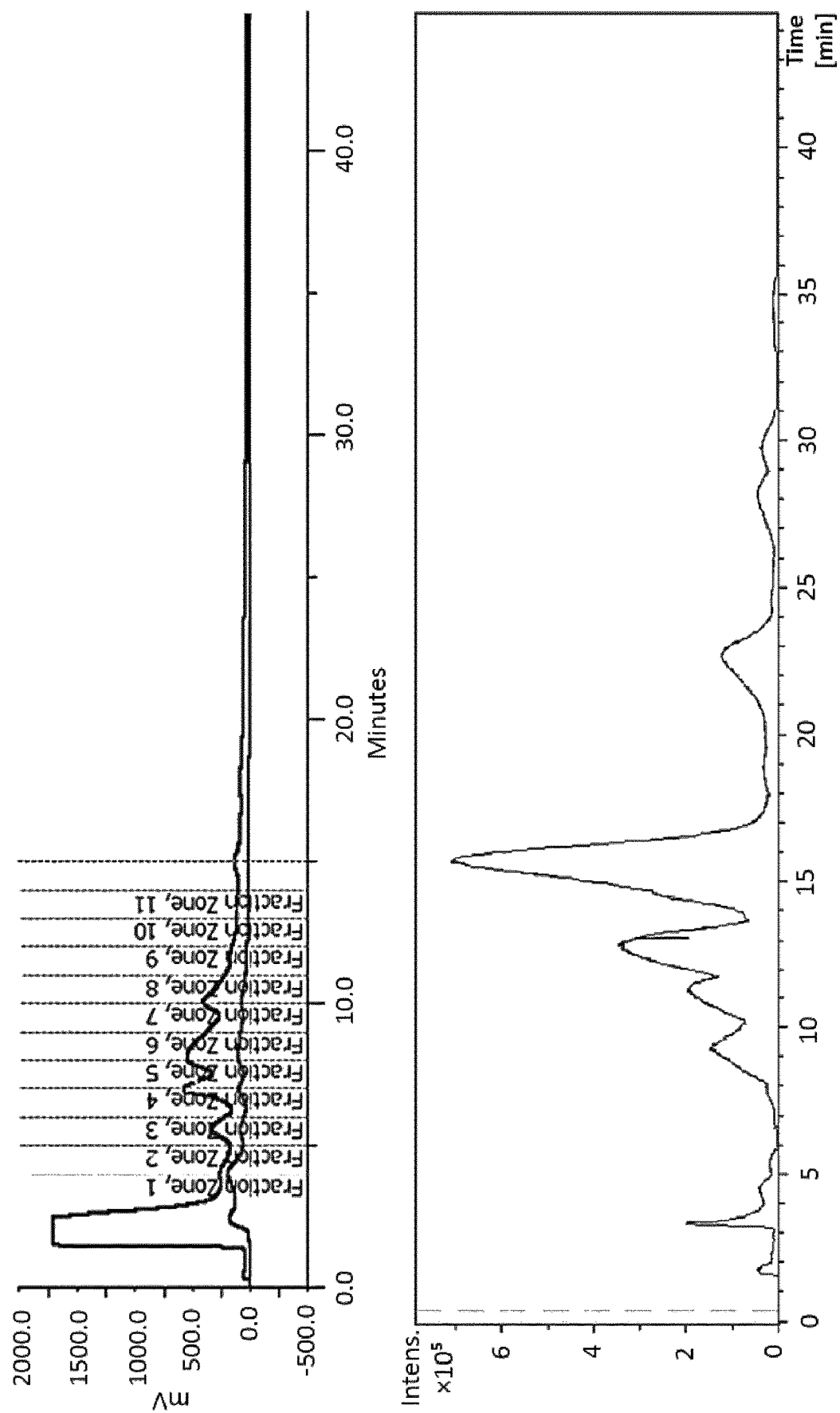

FIG. 2. Semi-preparative chromatograms by HPLC-UV with collection and TOF-MS.

Figure 3A:
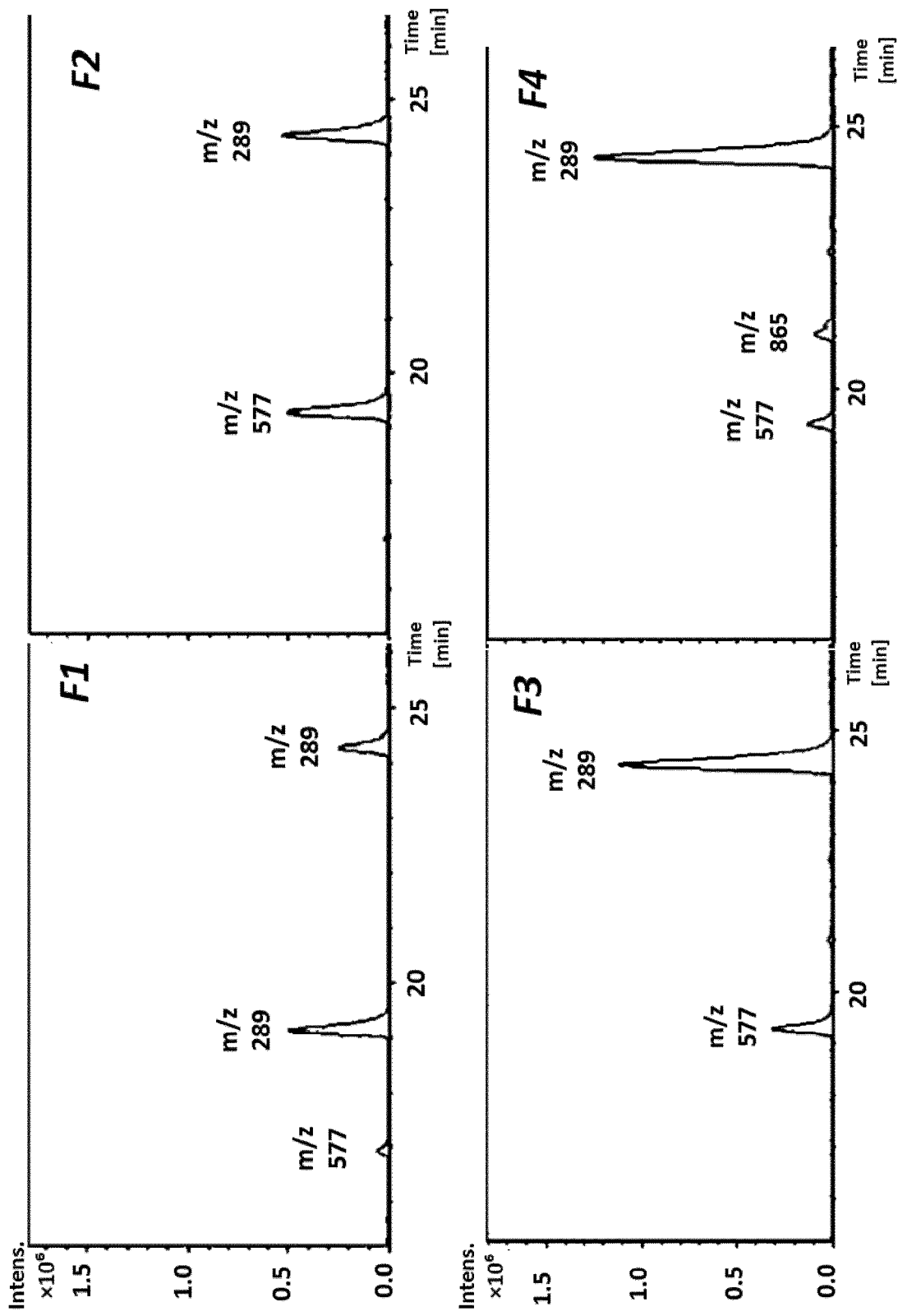
Figure 3B:
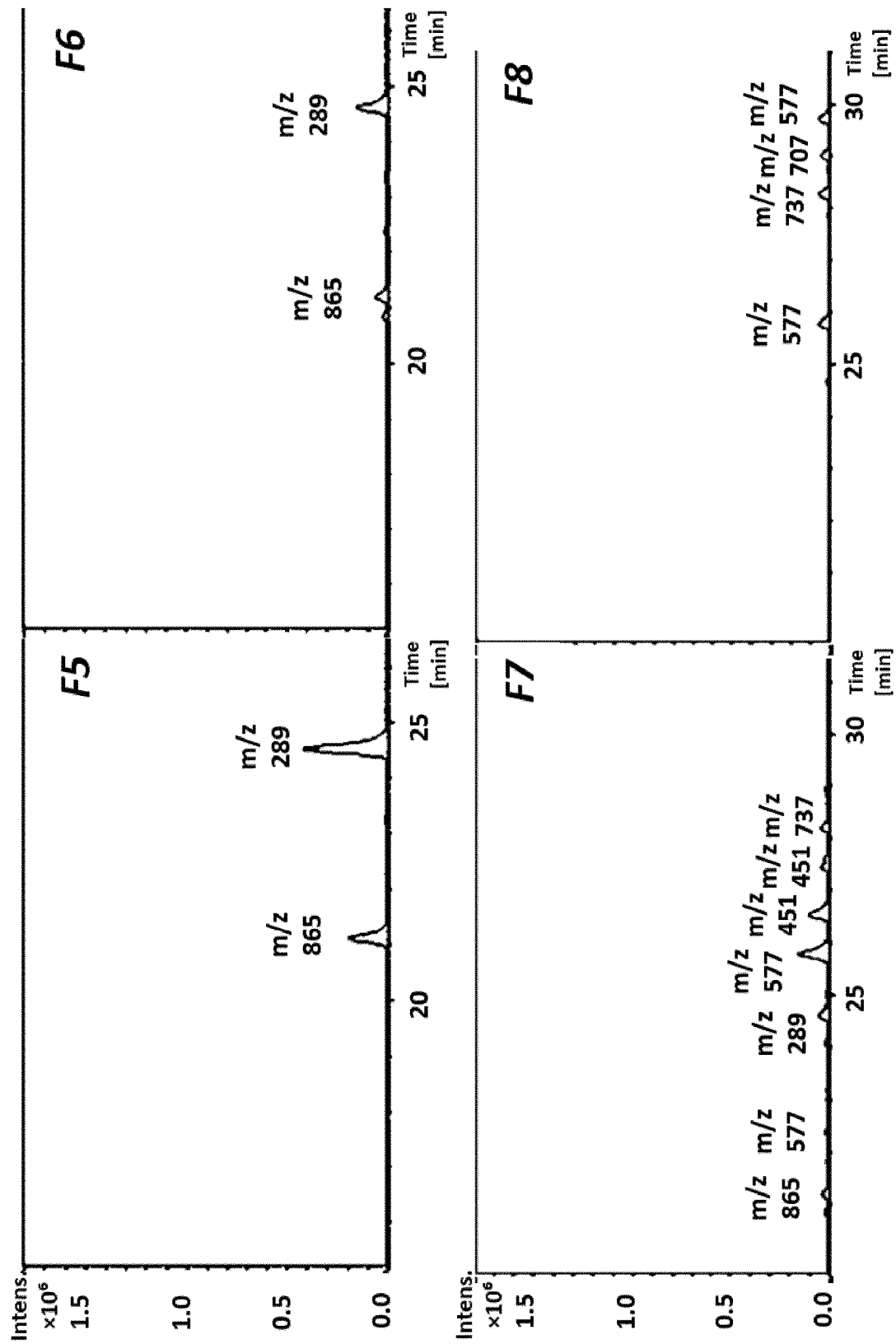
Figure 3C:
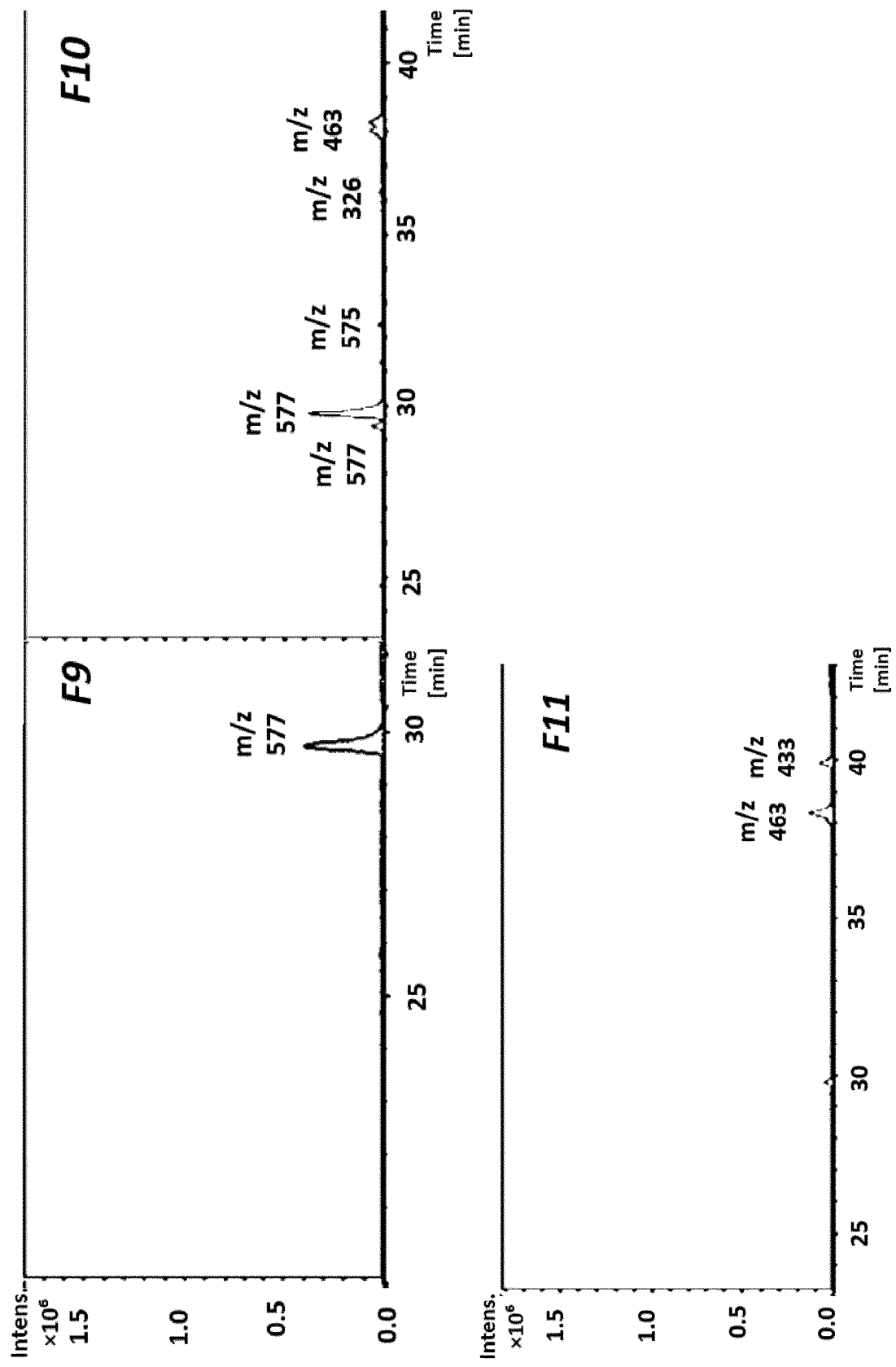

FIG. 3 (A, B, C). BPC of eleven obtained fractions from PC Sep-Pak fraction by HPLC-ESI-TOF-MS.

Figure 4:
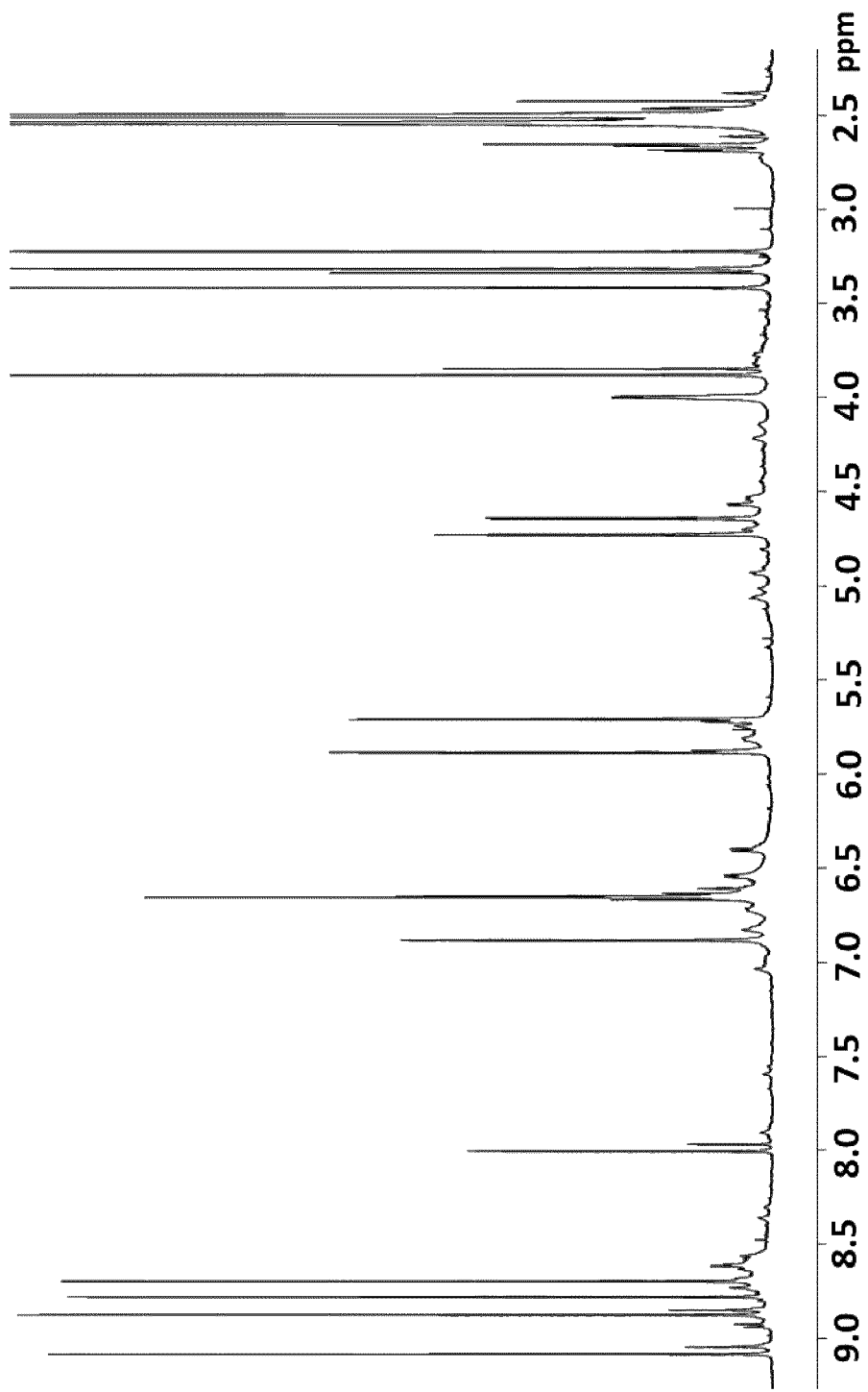

FIG. 4. NMR 1H spectra in DMSO-d6 of F5 from cacao extract.

Figure 5:
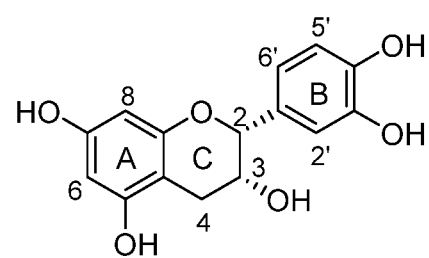

FIG. 5. Chemical structure of (−)-epicatechin.

Figure 6:
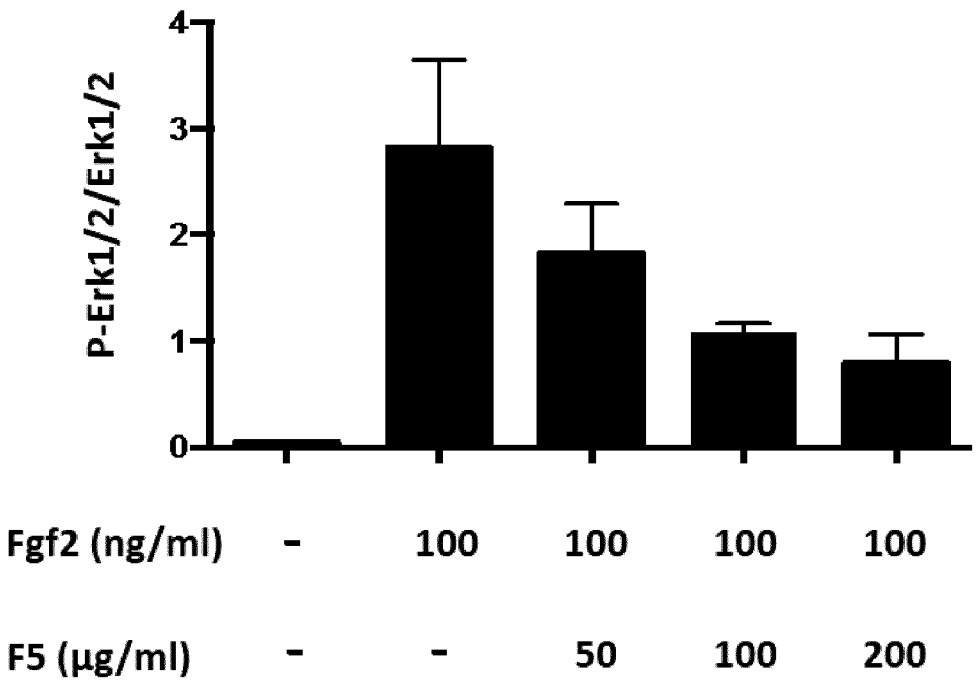

FIG. 6. Dose related inhibition of Erk1/2 phosphorylation in TD chondrocyte lines using FGF2 (100 ng/ml) and fraction 5 (50-100-200 μg/ml).

Figure 7:
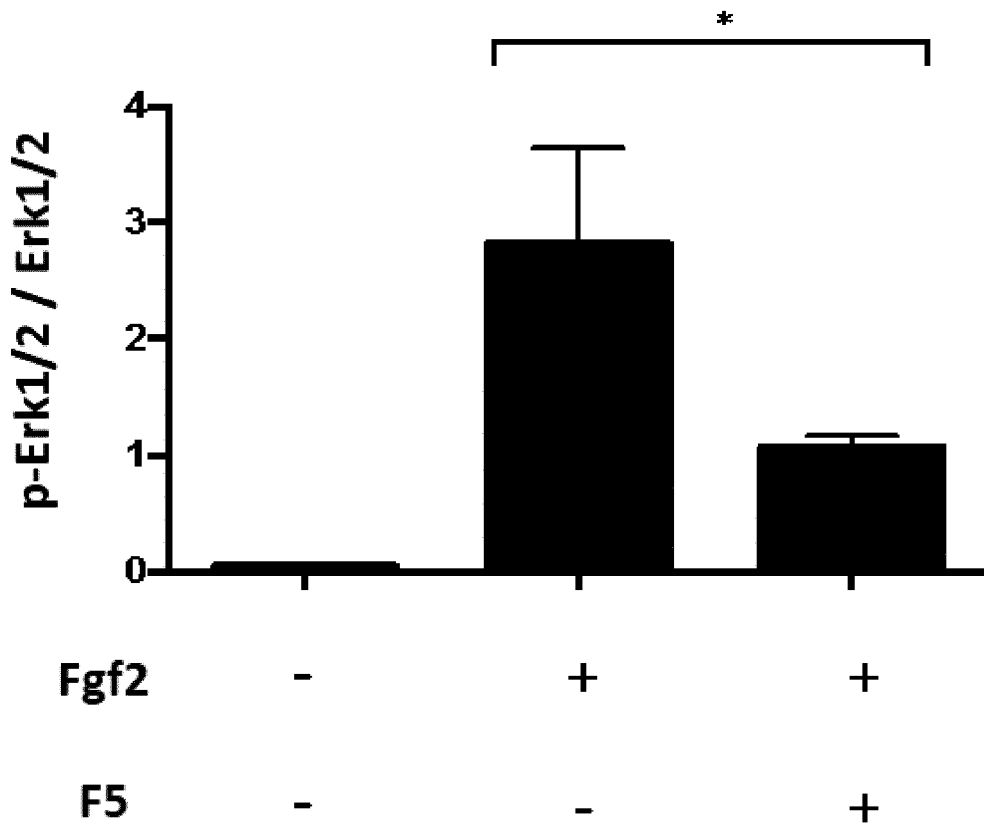

FIG. 7. Representative data of treatments of TD human chondrocyte lines using FGF2 (100 ng/ml) and fraction 5 (100 μg/ml). p* 0.0212

Figure 8:
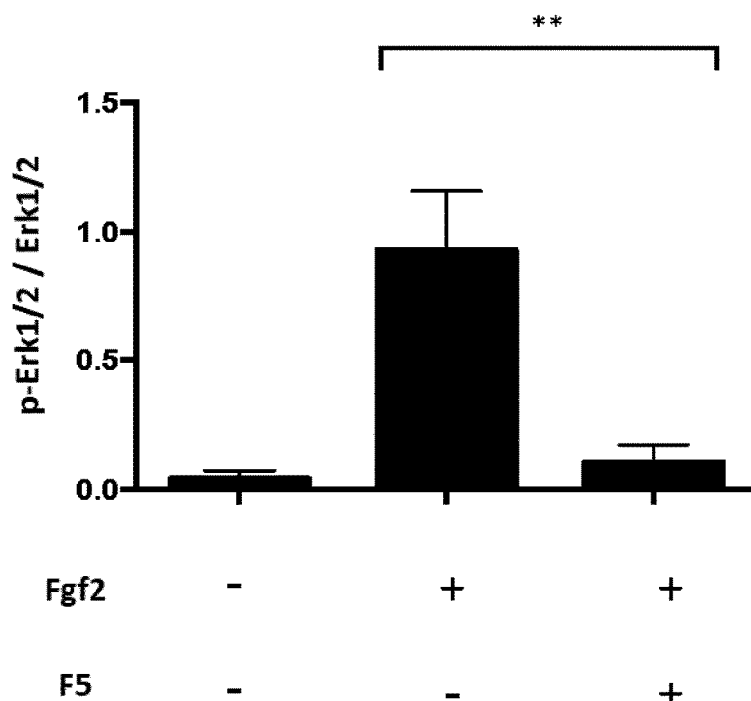

FIG. 8. Representative data of treatments of ACH human chondrocyte lines using FGF2 (100 ng/ml) and fraction 5 (100 μg/ml). p** 0.0038

Figure 9:
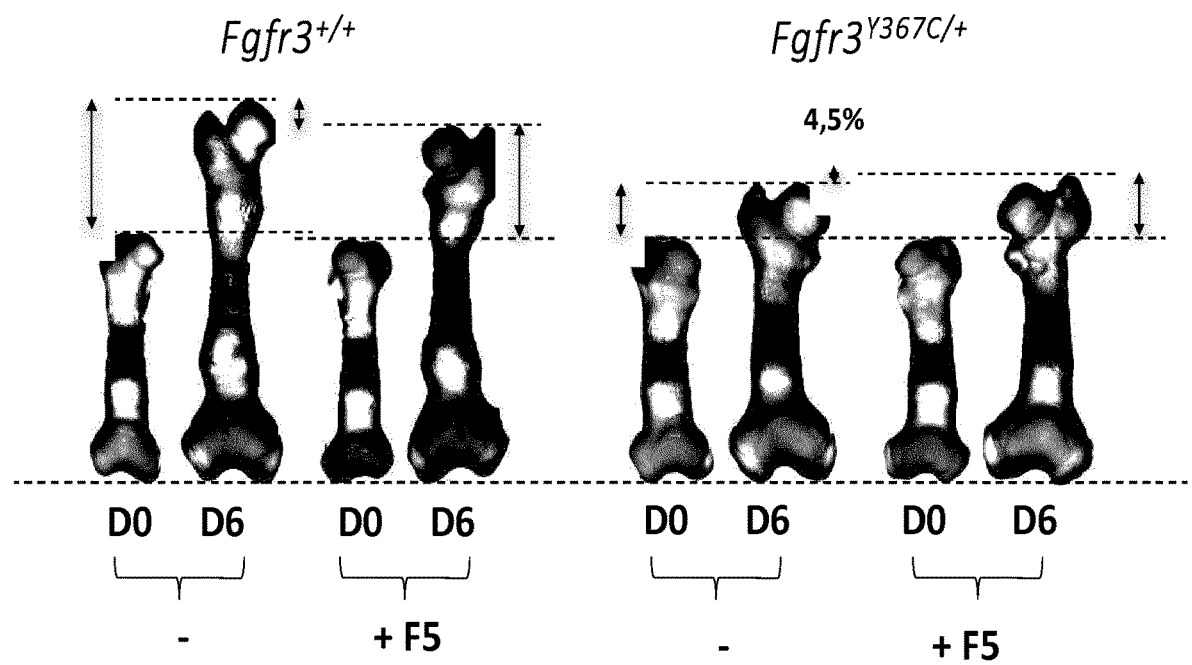

FIG. 9. Representative picture of femurs treated with fraction 5 (10 μg/ml).

Figure 10:
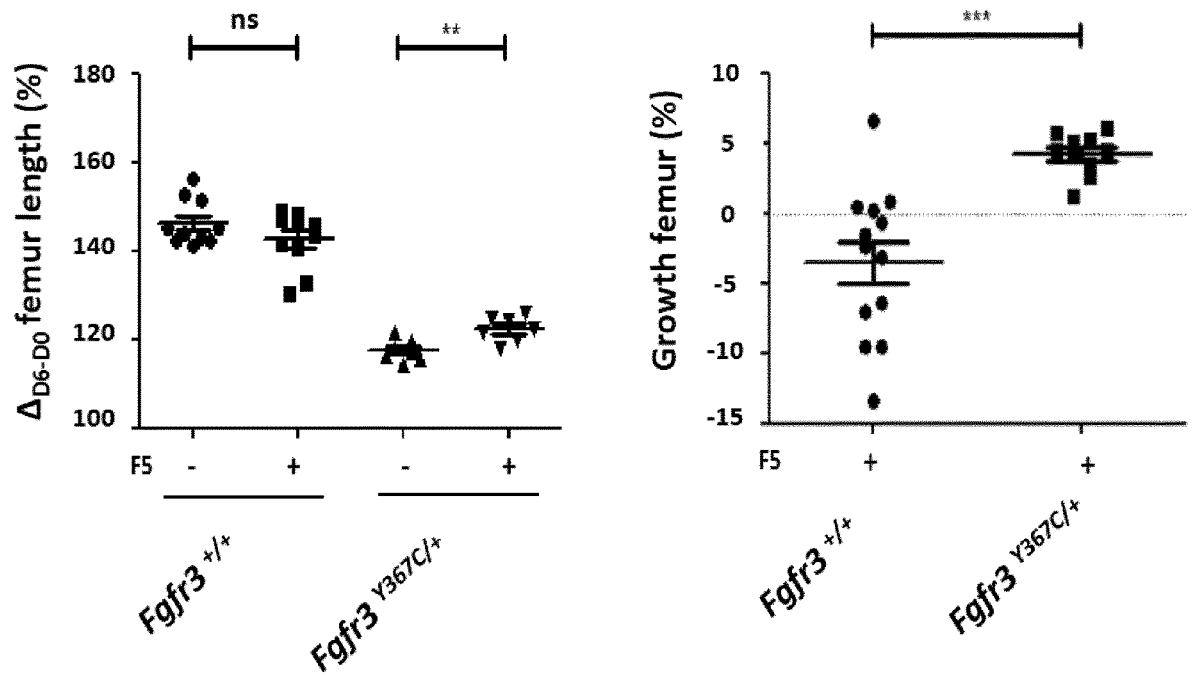

FIG. 10. Graphic representation of femur length and % of growth of the femurs treated with F5 (10 μg/ml).

Figure 11:
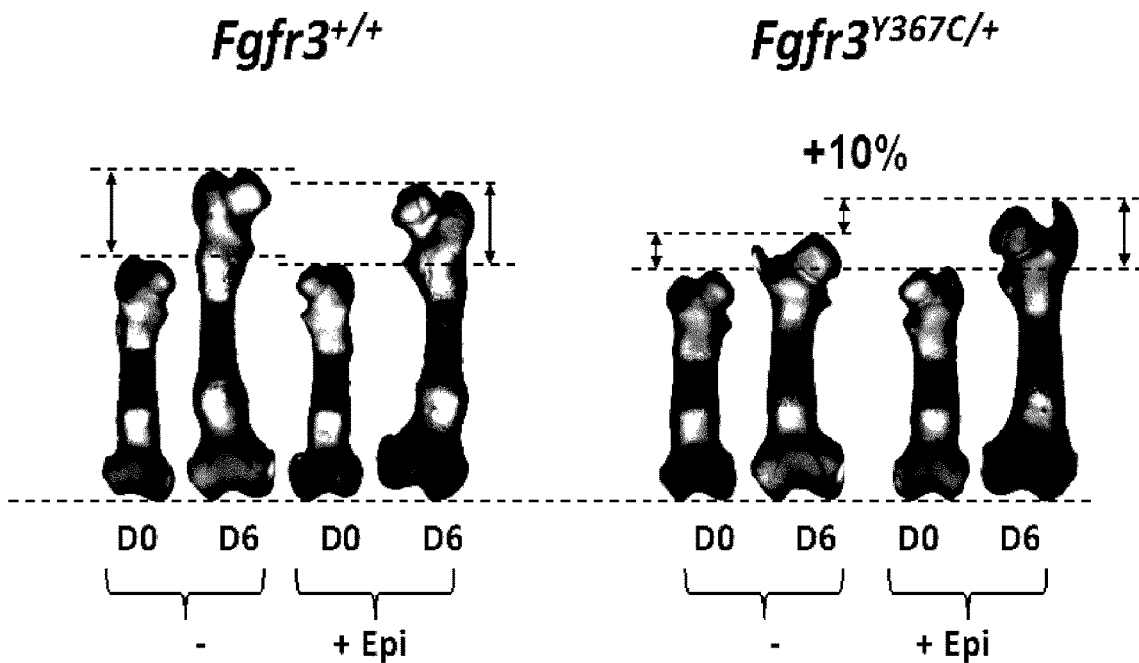

FIG. 11. Representative picture of femurs treated with (−)-epicatechin (10 μg/ml).

Figure 12:
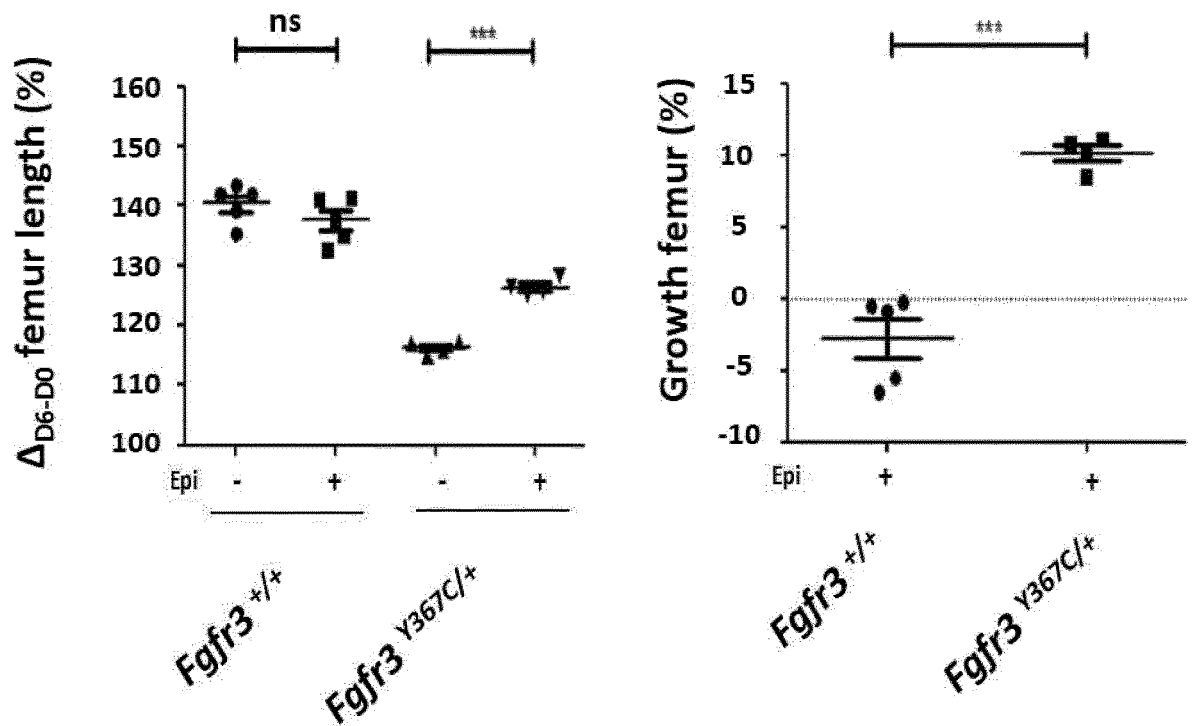

FIG. 12. Graphic representation of femur length and % of growth of the femurs treated with (−)-epicatechin (10 μg/ml).

Figure 13:
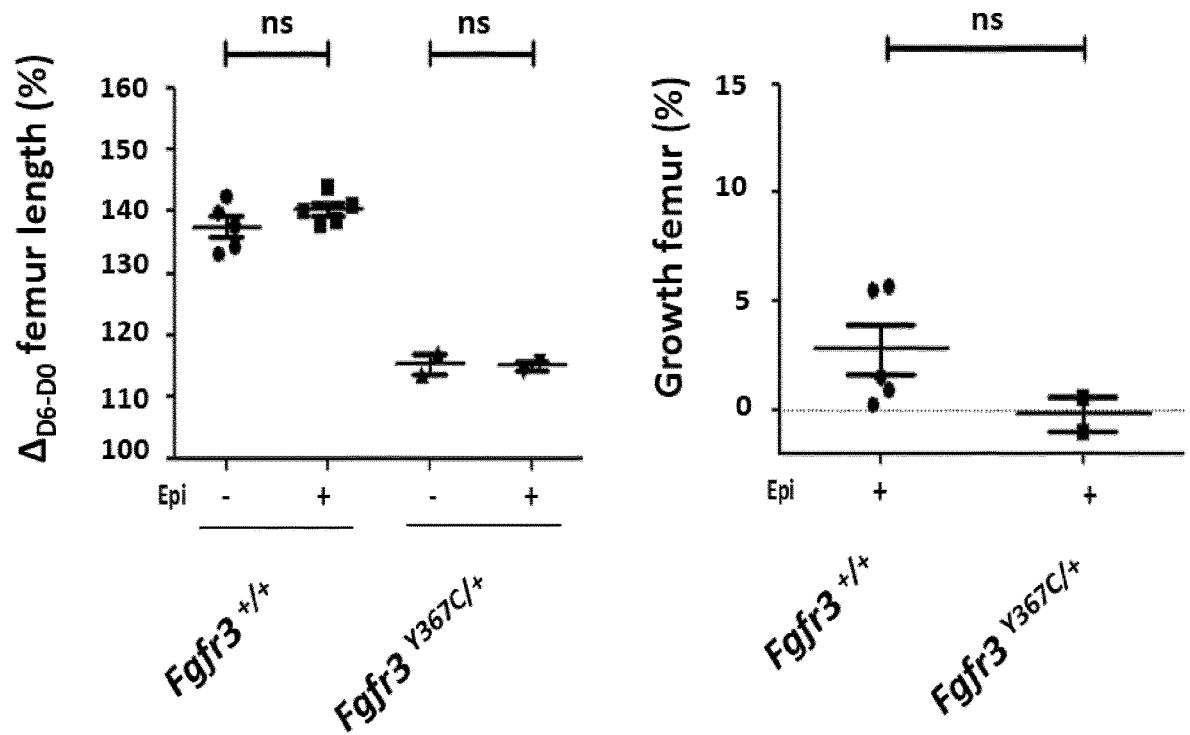

FIG. 13. Graphic representation of femur length and % of growth of the femurs treated with (−)-epicatechin (1 μg/ml).

Figure 14:
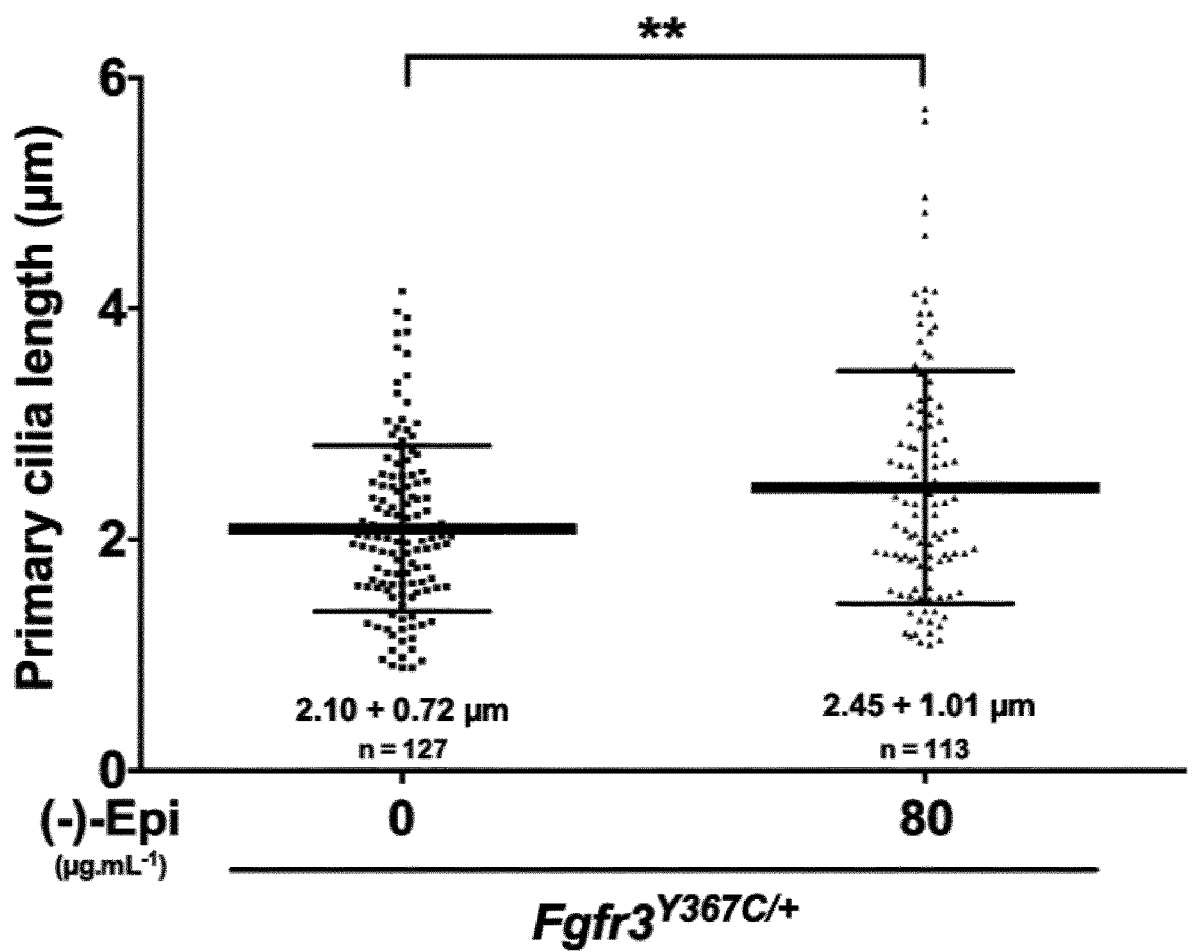

FIG. 14. Primary cilium elongation by (−)-epicatechin in antenatal E16.5 chondrocytes

EXAMPLE

Methods

1. Chemicals and Reagents.

All chemicals were of HPLC-MS grade and used as received. Acetic acid and methanol for HPLC and semi-preparative were purchased from Fluka (Sigma-Aldrich, Steinheim, Germany) and Lab-Scan (Gliwice, Sowinskiego, Poland), respectively. Diethyl ether and methanol for extraction were purchased from Fisher (Fisher Scientific Co., Fair Lawn, NJ), ethyl acetate from Lab-Scan (Gliwice, Sowinskiego, Poland), ethanol and acetone from AnalaR Normapur (VWR International, Inc., Darmstadt, Germany) and dimethyl sulfoxide (DMSO) was purchased from Panreac (Barcelona, Spain) for analytical assays. (−)-epicatechin was purchased from Sigma-Aldrich (St Louis, MO, USA). Water was purified by a Milli-Q system from Millipore (Bedford, MA, USA). Deuterated solvents such as dimethylsulfoxide were purchased from Eurisotop (France). For NMR analysis, the sample was dissolved in dimethylsulfoxide-d6 and transferred in an oven-dried 5 mm NMR tube for spectral analysis.

Waters 5 g Sep-Pak C18 Plus cartridges (Mildford, USA) were used as solid-phase extraction minicolumns for purification and concentration.

2. Sample Preparation.

A concentrated *T. cacao* extract was used in this study (Molteoleder, Spain). The polyphenols from whole cocoa matrix were analytically characterized using a solution of cocoa extract of 10 mg/mL in DMSO.

For cartridges purification, a solution stock of 0.1 g/mL was prepared by dissolving the appropriate amount of cacao extract in DMSO. The sample was sonicated for 5 min, vortexed for 1 min, and then centrifuged for 5 min at 7700 g before the cartridges purification.

For semi-preparative HPLC purification, a solution stock of 75 mg/mL was prepared by dissolving the PC fraction of C18 Sep-Pak cartridges in DMSO. The sample was sonicated for 5 min, vortexed for 1 min, and then centrifuged for 5 min at 7700 g before the semi-preparative HPLC analysis.

Each obtained sample was filtered through a 0.25 mm filter before the preparative HPLC analysis.

3. Instrumentation.

The polyphenols from the PC fraction from Sep-Pak cartridges purification were fractionated using a Gilson preparative HPLC system (Gilson Inc., Middleton, WI, USA) equipped with a binary pump (model 331/332), automated liquid handling solutions (model GX-271) and UV-Vis detector (model UV-Vis 156).

*T. cacao* and isolated fractions were analytically characterized using an Agilent 1200 series rapid-resolution LC system (AgilentTechnologies, Palo Alto, CA, USA) equipped with a binary pump, an autosampler and a diode-array detector (DAD). The HPLC system was coupled to a time-of-flight (TOF) mass spectrometer (Bruker Daltonics, Bremen, Germany) equipped with an electrospray ionization (ESI) interface (model G1607A from Agilent Technologies, Palo Alto, CA).

4. Fractionation of Polyphenols for Obtaining of (−)-Epicatechin from *T. cacao* Extract.

4.1. By Sep-Pak C18 Cartridges.

*T. cacao* extract prepared as describe above in sample preparation section was fractionated by Waters C18 Sep-Pak cartridges following the method describe by Sun et al. (Sun et al., 2006) and Monagas et al. (Monagas et al., 2003) with some modifications. Five different fractions were obtained: phenolic acids (PA fraction), monomeric and oligomeric flavan-3-ols (PC fraction), polymeric proanthocyanidins (PP fraction), monomers (MN fraction) and oligomers (OL fraction).

The experiments were performed in triplicate to ensure the repeatability of the fractionation by the cartridges.

The five obtained fractions were evaporated to dryness under vacuum in Speed Vac. The residue of each one was weighted and dissolved in DMSO at 100 μg/mL. After that, they were filtered through a 0.25 μm filter to analyze them by HPLC-ESI-TOF-MS.

4.2. By Combination of Sep-Pak and Semi-Preparative HPLC.

The compounds from PC fraction from C18 cartridges were fractionated according to Cádiz-Gurrea et al. (Cádiz-Gurrea et al., 2014). Finally, a total of 11 fractions were collected and the solvent was evaporated under vacuum. The residue of each fraction was weighted and dissolved with an appropriate volume of DMSO at concentration level of 100 μg/mL. Finally, all fractions were filtered through a 0.25 μm filter before the HPLC analysis.

5. Chromatographic Conditions and ESI-TOF-MS Detection.

The compounds from the *T. cacao* and fractions were separated following the method described by Cádiz-Gurrea et al. (Cádiz-Gurrea et al., 2014) with this modifications: the HPLC system was coupled to a TOF mass spectrometer equipped with an ESI interface operating in negative ion mode using a capillary voltage of +3.5 kV. The other optimum values of the source parameters were: drying gas temperature, 200° C.; drying gas flow, 10 L/min; and nebulizing gas pressure, 2.3 bar. The detection was performed considering a mass range of 50-1200 m/z.

The samples were injected in triplicate to ensure the repeatability of the analysis.

6. NMR Conditions.

NMR spectra was recorded at 293±0.1 K on a Bruker Avance III 600 spectrometer operating at a proton frequency of 600.13 MHz using a 5 mm QCI quadruple resonance pulse field gradient cryoprobe. The multiplicities observed are labeled as s=singlet; d=doublet; dd=doublet of doublets; t=triplet; m=multiplet; and bs=broad singlet. The sample was measured, without rotation and using 8 dummy scans prior to 128 scans. Acquisition parameters have been set as follows: size of fid=64 K, spectral width=20.5 ppm, acquisition time=2.73 s, relaxation delay=10 s, receiver gain=20.2, FID resolution=0.25 Hz. A pre-saturation pulse sequence (Bruker 1D noesygppr1d) was used to suppress the residual $H_2O$ signal via irradiation of the $H_2O$ frequency during the recycle and mixing time delays. The resulting spectrum was automatically phased, baseline-corrected, and calibrated to the TSP signal at 0.0 ppm. The t1 time was set to 4 us and the mixing time (d8) to 10 ms. The spectrometer transmitter was locked to DMSO-d6 frequency. Acquisition and processing of spectra were carried out with TOPSPIN software (version 3.1). 1H-1H total correlation spectroscopy (TOCSY), 1H-13C heteronuclear single quantum coherence (HSQC), 1H-13C heteronuclear multiple bonds coherence (HMBC) spectra were recorded using standard Bruker sequences. The TOCSY spectrum was obtained applying a relaxation delay of 2.0 s, spectral width in both dimensions of 7194.25 Hz and a receiver gain of 64.0. TOCSY spectrum was processed using sine-bell window function (SSB=2.0). The HSQC spectrum was acquired using a relaxation delay of 1.0 s, spectral width of 7211.54 Hz in F2 and 24900.71 Hz in F1. Quadratic sine window function (SSB=2.0) was used for the HSQC spectrum. The HMBC spectrum was recorded with the same parameters used in the HSQC spectra except for 37729.71 Hz of spectral width in F1. The coupling constant for HSQC experiment was fixed to 145 Hz whereas HMBC experiment was obtained using fixed coupling constants of 145 and 8 Hz (long range).

7. Evaluation of the Efficacy of F5 with Human Chondrocyte Lines Expressing FGFR3 Gain-of-Function Mutations The F5 from cocoa extract was evaluated in vitro using chondrocyte lines expressing human FGFR3 gain-of-function mutations. We have studied two human chondrocyte lines, the first one expresses the heterozygous achondroplasia (ACH) mutation (Gly380Arg) and the other one the heterozygous thanatophoric dysplasia (TD) mutation (Tyr373Cys) (Benoist-Lasselin C. et al. FEBS Lett. 2007).

The cells were depleted during 24 hours, we tested various concentrations (50, 100, 200 μg/ml) of F5 from cocoa. The cocoa fraction was added in the medium then the cells were stimulated with a ligand of the receptor FGF2 (Fibroblast Growth Factor). The efficacy of the cocoa fraction on the activation of FGFR3 was evaluated by western blotting (n=3). We evaluated the level of phosphorylation of Erk1/2, two proteins of the canonical Mapkinase pathway.

The levels of phosphorylated Erk1/2 and Erk1/2 were measured using the Li-Cor technology and Imager.

8. Evaluation of the Efficacy of Fraction 5 from Cacao Extract and (−)-Epicatechin on Ex Vivo Femur Cultures Isolated from Fgfr3$^{Y367C/+}$ Mice Heterozygous Fgfr3$^{Y367C/+}$ mice ubiquitously expressing the Y367C mutation and exhibiting a severe dwarfism were used (Pannier et al., Biochim Biophys Acta, 1792: 140-147, 2009, Pannier S et al. Bone 47: 905-915, 2010). Several sets of ex vivo experiments were performed as previously described (Jonquoy et al., Hum Mol Genet, 21: 841-851, 2012). Femur embryos at day E16.5 from Fgfr3$^{+/+}$ (n=23) and Fgfr3$^{Y367C/+}$ (n=16) mice were used and incubated for 6 days in DMEM medium with antibiotics and 0.2% BSA (Sigma) supplemented with cocoa F5 or (−)-epicatechin (Sigma-0394-05-90) or DMSO (as control) at a concentration of 10 and 30 μg/ml. To establish the effect of the inhibitors, the left femur was cultured in supplemented medium and compared with the right one cultured in control medium. The bone length was measured at the beginning (before treatment) and at the end of time course. The genotype of Fgfr3$^{+/+}$ and Fgfr3$^{Y367C/+}$ mice were determined by PCR of tail DNA as previously described (Pannier et al., Biochim Biophys Acta, 1792: 140-147, 2009). All experimental procedures and protocols were approved by the Animal Care and Use Committee.

9. Evaluation of the Efficacy of Fraction 5 from Cacao Extract and (−)-Epicatechin on Growth Plate Cartilage In order to appreciate the impact of the treatment on the growth plate cartilage, we performed histological and immunohistological studies. We selected specific markers of the cartilage, SOX9 and Collagen type X, we tested the expression of the protein FGFR3 and we also evaluated the expression of the phosphorylated Erk1/2 proteins of the Mapkinase signalling and activated by FGFR3.

Limb explants were fixed after culture in 4% paraformaldehyde at 4° C. and embedded in paraffin. Serial 5 μm sections were stained with Hematoxylin-Eosin using standard protocols for histological analysis or were subjected to immunohistochemical staining.

For immunohistochemistry, sections were stained with antibodies specific to FGFR3 (1:100 dilution; Sigma), anti-Collagen type X (1:50 dilution; Quartett) anti-SOX9 (1:1000 dilution; Abcam), anti-phosphorylated Erk1/2 (1:100 dilution; Cell signaling) using the Dako Envision system kit. Images were captured with an Olympus PD70-IX2-UCB microscope.

10. Immunocytochemistry

Cultured chondrocytes issued from Fgfr3$^{Y367C/+}$ were fixed at room temperature for 10 min in methanol (chilled at −20° C.), and then washed with PBS. Samples were permeabilized for 10 min with PBS containing 0.1% Triton-X100 (Sigma-Aldrich), then washed three times for 5 min. Samples were incubated with PBS containing 10% goat serum (Biowest) for 60 min at room temperature. Primary antibodies were incubated at 4° C. overnight. The following primary antibodies were used: mouse IgG1 anti-γ-tubulin (Sigma-Aldrich #T6557, 1:1000) and rabbit anti-Arl13b (Proteintech #177111-AP, 1:500). Cells were washed with PBS, and then incubated with goat anti-mouse IgG1 coupled with AlexaFluor 488 (Life Technologies, 1:1000) and goat anti-rabbit coupled with AlexaFluor 647 (Life Technologies, 1:1000) secondary antibodies for 2 h at room temperature in the dark. Samples were extensively washed and mounted with a solution of DAPI-Fluoromount G (SouthernBiotech) containing DAPI (4',6'-diamidino-2-phenylindole) for nuclear staining.

Image acquisition were captured using a Spinning disk confocal microscope. The system is composed by a Yokogawa CSU-X1 spinning disk scanner coupled to a Zeiss Observer Z1 inverted microscope and controlled by Zen Blue software. Tile images were acquired with a Plan Apochromat 63× oil immersion objective (NA 1.46) through a Hamamatsu Orca Flash 4.0 sCMOS Camera. In order to compare measured data, all confocal experiments showing PC length was acquired in same conditions using slice thickness of 0.20 μm and a pixel size of 60 nm. Post-treatment analyses were performed with FIJI (Fiji Is Just ImageJ; NIH) and Imaris v8.3 software (Bitplane). We performed 25 images per Z-stack and realized a Z-projection with maximal intensity. We next measured in 2D the PC lengths by IMARIS software (Bitplane).

Results

1. Comprehensive Characterization of Fractions by HPLC-ESI-TOF-MS.

The FIG. 1 showed the different profiles (base peak chromatograms and characterized compounds), which were obtained by Sep-Pak C18 cartridges. This proposed method permitted separating phenolic compounds from the whole *T. cacao* extract into various different fractions, which were less complex, enabling their use in order to achieve pure fractions of interested compounds. In addition, eleven fractions were obtained by combination of solid phase extraction by Sep-Pak C18 cartridges and semi-preparative HPLC isolation in order to obtain purified fractions of monomeric and oligomeric PAs (FIG. 2). The composition of each one was established by the detailed HPLC-ESI-TOF-MS (FIGS. 3 A, B and C). Only in F1 we could find (+)-catechin (by comparing to the commercial standard) and (−)-epicatechin (m/z 289). In F2 and F3, there are a B-type dimer or PC and (−)-epicatechin, the last one was presented with high intensity in F3. Moreover, a PC trimer appeared in fractions from 4 to 7 (m/z 865). Less purified fractions were F7, F8 and F10 with four or more compounds. However, a B-type dimer of PC was detected in F9 being the most purify fraction.

After preliminary biological tests of the obtained fractions, F5 was selected as a candidate for the biological experiments in achondroplasia model.

2. NMR Identification of Compounds from Selected F5.

FIG. 4 showed the $^1$H spectra in DMSO-d6 for F5 where the most abundant compound corresponded to (−)-epicatechin (FIG. 5).

Table 1 contains the $^1$H and $^{13}$C NMR data obtained in this work for (−)-epicatechin in F5 from cacao sample. The identification of similar substances as (+)-catechin and (−)-epicatechin was carried out on the basis of the spectroscopic data of aliphatic protons H-3(C) and H-2(C). High values of the coupling constant $^3J_{2,3}$ (8-10 Hz) indicate the presence of (+)catechin, whereas $^3J_{2,3}$ values round 2 Hz or broad singlet demonstrated the presence of (−)-epicatechin in our cacao fraction.

TABLE 1

$^1$H and $^{13}$C NMR chemical shift data for (−)-epicatechin from F5 in d$_6$-DMSO.

| Ring | Position | $^{13}$C δ(ppm) | $^1$H δ(ppm) | multiplicity | Coupling constant data (Hz) |
|---|---|---|---|---|---|
| A | 6 | 94.54 | 5.71 | d | 2.3 |
| A | 8 | 95.52 | 5.89 | d | 2.3 |
| B | 5' | 115.21 | 6.66 | d | 8.0 |
| B | 6' | 118.41 | 6.65 | dd | 1.6; 8.0 |
| B | 2' | 115.36 | 6.89 | d | 1.6 |
| C | 2 | 78.52 | 4.73 | s (br) | — |
| C | 3 | 65.37 | 4.00 | m | — |
| C | 4 | 28.67 | 2.67 | dd | 4.6; 16.5 |
| C | 4 | 28.67 | 2.47 | dd | 3.5; 16.5 | d = doublet,
dd = double doublet;
s (br) = broad singlet;
m = multiplet

3. Evaluation of the Efficacy of F5 on the Mapkinase Pathways Using Human Chondrocyte Lines Expressing FGFR3 Gain-of-Function Mutations We evaluated the level of phosphorylation of the protein Erk1/2, two specific proteins of the Mapkinase pathway, by in vitro assays using human TD chondrocyte lines and F5 (50, 100, 200 μg/ml) and Fgf2 (100 ng/ml). Considering the data obtained (FIG. 6), we decided to treat the TD and ACH lines with 100 μg/ml of F5.

The treatment of the TD chondrocyte lines with F5 (100 μg/ml), showed a strong reduction of the level of Erk1/2 phosphorylation (FIG. 7). We tested also F5 (100 μg/ml) with ACH chondrocyte lines. A significant reduction of Erk1/2 phosphorylation was observed for this fraction in ACH cells (FIG. 8).

4. Evaluation of the Efficacy of F5 from Cacao Extract and (−)-Epicatechin on Ex Vivo Femur Cultures Isolated from Fgfr3$^{Y367C/+}$ Mice Mimicking Achondroplasia Regarding the data obtained in vitro and the data of the NMR analysis, we tested F5 and (−)-epicatechin in femur cultures.

F5 has been evaluated for a concentration of 10 μg/ml. The percentage of femur growth was more important in Fgfr3$^{Y367C/+}$ mice than in the Fgfr3$^{+/+}$ mice. F5 significantly increased the length of the Fgfr3$^{Y367C/+}$ femurs comparing to Fgfr3$^{+/+}$ femurs (FIG. 9). F5 did not impair the growth of the Fgfr3$^{+/+}$ femurs (FIG. 10).

Considering the data of NMR, we evaluated the efficacy of (−)-epicatechin on bone growth using two different concentrations: 1 and 10 μg/ml.

(−)-Epicatechin (10 μg/ml) significantly increased the length (+10%) of the Fgfr3$^{Y367C/+}$ femurs comparing to Fgfr3$^{+/+}$ femurs (FIG. 11). The percentage of femur growth was more important in Fgfr3$^{Y367C/+}$ mice than in the Fgfr3$^{+/+}$ mice. (−)-Epicatechin (10 μg/ml) did not impair the growth of the Fgfr3$^{+/+}$ femurs (FIG. 12).

The data obtained with (−)-epicatechin with a lower concentration (1 μg/ml) did not improve the size of the femurs for Fgfr3$^{Y367C/+}$ and Fgfr3$^{+/+}$ (FIG. 13).

5. Evaluation of the Efficacy of F5 from Cacao Extract and (−)-Epicatechin on Growth Plate Cartilage The immunohistological analyses showed a slight modification of the collagen type X expression in proximal and distal femurs treated with F5. We noted a decreasing expression of FGFR3 and SOX9. There was no obvious modification of phosphorylated Erk1/2 expression in the distal and proximal femurs. The analyses of the both proximal and distal femur did not show obvious modification of the epiphysis size.

Studying the H&E staining, we observed that the (−)-epicatechin treatment improved the whole growth plate cartilage. We noted an increase size of the epiphysis (data not shown). The gain-of-growth is labelled with red arrows. In the distal part of the femurs, the improvement of the size of the epiphysis was more obvious (data not shown). The reserve, proliferative and pre-hypertrophic zones of the growth plate cartilage were increased.

The expression of collagen type X was not modified in proximal and distal femurs, while the expressions of FGFR3 and Sox9 were strongly decreased in proximal and distal femurs. Interestingly, the phosphorylated Erk1/2 expression was slightly decreased in proximal and distal femurs treated with (−)-epicatechin.

6. Primary Cilum Elongation by (−)-Epicatechin in Antenatal E16.5 Chondrocytes

FIG. 14 showed a graphical representation of length of the average primary cilium Fgfr3$^{Y367C/+}$ chondrocytes with and without (−)-Epicatechine treatment (n>100). The data represent mean+S.E.M., two-tailed unpaired t-test. ns, not significant; *p<0.05, *p<0.001, **p<0.0001. n is the number of primary cilium measured, N is the number of cultured chondrocytes analyzed, A is the average of the length of the primary cilium. Values obtained and observed were N=3 and n=127 and n=113 for Fgfr3$^{Y367C/+}$ chondrocytes treated without and with (−)-Epicatechin, respectively. Primary cilium average observed were A=2.10+0.06 and A=2.45+0.09 for Fgfr3$^{Y367C/+}$ chondrocytes treated without and with (−)-Epicatechin, respectively. The addition of (−)-epicatechin leads to an elongation of primary cilium.

REFERENCES

Throughout this application, various references describe the state of the art to which this invention pertains. The disclosures of these references are hereby incorporated by reference into the present disclosure.

Andújar, I., Recio, M. C., Giner, R. M., Rios, J. L., 2012. Cocoa Polyphenols and Their Potential Benefits for Human Health. Oxid. Med. Cell. Longev. 2012, 1-23. doi:10.1155/2012/906252

Benoist-Lasselin C, Gibbs L, Heuertz S, Odent T, Munnich A, Legeai-Mallet L. 2007 Human immortalized chondrocytes carrying heterozygous FGFR3 mutations: an in vitro model to study chondrodysplasias. FEBS Lett. 2007 Jun. 12; 581(14):2593-8. DOI:10.1016/j.febslet.2007.04.079

Borrego, E., Farrington, D. M., Downey, F. J., 2014. Novedades en displasias óseas. Rev. Esp. Cir. Ortop. Traumatol. doi:10.1016/j.recot.2013.12.001

Cádiz-Gurrea, M. de la L., Fernandez-Arroyo, S., Joven, J., Menéndez, J. A., Micol, V., Segura-Carretero, A., 2015. Proanthocyanidins in Agro-Industrial By-Products: Health Benefits, in: Motohashi, N. (Ed.), Occurrences, Structure, Biosynthesis, and Health Benefits Based on Their Evidences of Medicinal Phytochemicals in Vegetables and Fruits. Volume 3. pp. 63-114.

Cádiz-Gurrea, M. de la L., Lozano-Sánchez, J., Contreras-Gámez, M. del M., Legeai-Mallet, L., Fernandez-Arroyo, S., Segura-Carretero, A., 2014. Isolation, comprehensive characterization and antioxidant activities of Theobroma cacao extract. J. Funct. Foods 10, 485-498. doi:10.1016/j.jff.2014.07.016

Di Rocco, F., Duplan, M. B., Heuzé, Y., Kaci, N., Komla-Ebri, D., Munnich, A., Mugniery, E., Benoist-Lasselin, C., Legeai-Mallet, L., 2014. FGFR3 mutation causes abnormal membranous ossification in achondroplasia. Hum. Mol. Genet. 23, 2914-2925. doi:10.1093/hmg/ddu004

He, F., Pan, Q.-H., Shi, Y., Duan, C.-Q., 2008. Biosynthesis and genetic regulation of proanthocyanidins in plants. Molecules 13, 2674-2703.

Horton, W. A., Hall, J. G., Hecht, J. T., 2007. Achondroplasia. Lancet 370, 162-172. doi: 10.1016/S0140-6736(07)61090-3

Huete, F., Guzman-Aranguez, A., Ortin, J., Hoyle, C. H. V, Pintor, J., 2011. Effects of diadenosine tetraphosphate on FGF9-induced chloride flux changes in achondroplastic chondrocytes. Purinergic Signal. 7, 243-249. doi:10.1007/s11302-011-9234-y Jonquoy A, Mugniery E, Benoist-Lasselin C, Kaci N, Le Corre L, Barbault F, Girard A L, Le Merrer Y, Busca P, Schibler L, Munnich A, Legeai-Mallet L. A novel tyrosine kinase inhibitor restores chondrocyte differentiation and promotes bone growth in a gain-of-function Fgfr3 mouse model. Hum Mol Genet. 2012 Feb. 15; 21(4):841-51. doi: 10.1093/hmg/ddr514

Lanaud, C., Motamayor, J.-C., Sounigo, O., 2003. Cacao, in: Hamon et al., P. (Ed.), Genetic Diversity of Cultivated Tropical Plants. Sci. Publisher, Inc. and Cirad, USA, pp. 125-156.

Legeai-Mallet, L., Segura-Carretero, A., 2015. *Theobroma cacao* extract for use in the treatment or prevention of receptor tyrosine kinases related disorders. WO2016046375 A1.

Monagas, M., Gómez-Cordovés, C., Bartolomé, B., Laureano, O., Ricardo Da Silva, J. M., 2003. Monomeric, Oligomeric, and Polymeric Flavan-3-ol Composition of Wines and Grapes from *Vitis vinifera* L. Cv. Graciano, Tempranillo, and Cabernet Sauvignon. J. Agric. Food Chem. 51, 6475-6481. doi:10.1021/jf030325+

Ornitz, D M., Legeai-Mallet, L; Achondroplasia: Development, pathogenesis, and therapy. Dev Dyn. 2017 April; 246(4):291-309. doi: 10.1002/dvdy.24479.

Orphanet, 2014. Prevalence of rare diseases: Bibliographic data. Orphanet Rep. Ser. 1-29.

Orphanet, n.d.: About Rare Diseases What is a rare disease? [WWW Document]. URL http://www.orpha.net/consor/cgi-bin/Education_AboutRareDiseases.php?lng=EN #

Pannier S, Couloigner V, Messaddeq N, Elmaleh-Bergès M, Munnich A, Romand R, Legeai-Mallet L. Activating Fgfr3 Y367C mutation causes hearing loss and inner ear defect in a mouse model of chondrodysplasia. Biochim Biophys Acta. 2009 February; 1792(2):140-7. doi: 10.1016/j.bbadis.2008.11.010.

Pannier S, Mugniery E, Jonquoy A, Benoist-Lasselin C, Odent T, Jais J P, Munnich A, Legeai-Mallet L. delayed bone age due to a dual effect of FGFR3 mutation in achondroplasia. Bone. 2010 November; 47(5):905-15. doi: 10.1016/j.bone.2010.07.020

Regulation (EC) No 141/2000 of the European Parliament and of the Council of 16 Dec. 1999 on orphan medicinal products, n.d.

Rodwell, C., Ayme, S., 2014a. 2014 Report on the State of the Art of Rare Disease Activities in Europe: 2014 Report on the State of the Art of Rare Disease Activities in Europe 1-68.

Rodwell, C., Ayme, S., 2014b. 2014 Report on the state of the art of the rare disease activities in Europe-Par I: overview of rare disease activities in Europe 1-68.

Rousseau F, Bonaventure J, Legeai-Mallet L, Pelet A, Rozet J M, Maroteaux P, Le Merrer M, Munnich A. Mutations of the fibroblast growth factor receptor-3 gene in achondroplasia. Nature. 1994 Sep. 15; 371(6494):252-4.

Sun, B., Leandro, M. C., de Freitas, V., Spranger, M. I., 2006. Fractionation of red wine polyphenols by solid-phase extraction and liquid chromatography. J. Chromatogr. A 1128, 27-38. doi:10.1016/j.chroma.2006.06.026

UniProt, n.d. P22607-FGFR3 HUMAN [WWW Document]. URL http://www.uniprot.org/uniprot/P22607

The invention claimed is:

1. A method of treating a FGFR3-related chondrodysplasia in a patient in need thereof comprising administering to the patient a therapeutically effective amount of a substantially pure (−)-epicatechin,
   wherein the step of administering comprises administering to the patient a pharmaceutical composition comprising the substantially pure (−)-epicatechin as an active principle and at least one pharmaceutically acceptable excipient, and
   wherein the pharmaceutical composition does not comprise a *Theobroma cacao* extract.

* * * * *